US00PP30478P2

(12) United States Plant Patent
Hansen

(10) Patent No.: US PP30,478 P2
(45) Date of Patent: May 7, 2019

(54) ***BAPTISIA* PLANT NAMED 'AMERICAN GOLDFINCH'**

(50) Latin Name: ***Baptisia* hybrid**
Varietal Denomination: American Goldfinch

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 15/732,696

(22) Filed: Dec. 15, 2017

(51) Int. Cl.
*A01H 5/02* (2018.01)

(52) U.S. Cl.
USPC ..... Plt./263.1

(58) Field of Classification Search
USPC ..... Plt./263.1
CPC ..... A01H 5/02
See application file for complete search history.

*Primary Examiner* — Keith O. Robinson

(57) ABSTRACT

A new and distinct cultivar of hardy herbaceous false indigo plant named *Baptisia* 'American Goldfinch' characterized by golden yellow flowers on long spikes maintaining their coloration from bud to anthesis. The new plant has a broad, mounded, multi-stemmed, winter-hardy habit with glaucous medium-green tri-foliate foliage and is suitable for landscaping as a specimen or en masse.

1 Drawing Sheet

Botanical classification: *Baptisia* hybrid.
Cultivar designation: 'American Goldfinch'.

BACKGROUND OF THE INVENTION

The present invention relates to a new and distinct cultivar of hybrid *Baptisia* plant, botanically known as *Baptisia* 'American Goldfinch' and will be referred to hereafter by its cultivar name, 'American Goldfinch'. The new cultivar represents a new false indigo, a hardy herbaceous perennial grown for landscape and cut flower use.

The new invention arose from an ongoing breeding program of the inventor at a nursery in Waseca, Minn. with continued evaluation at a wholesale perennial nursery in Zeeland, Mich. with the specific intention of improving garden worthiness of perennial false indigo plants with a wider variety of flower colors and improved garden habit.

*Baptisia* 'American Goldfinch' was a single seedling selection from a cross from a pollination of a proprietary unnamed unreleased hybrid of *B. sphaerocarpa* x *B. alba* (not patented) as the female or seed parent, and the male parent is an unnamed *Baptisia sphaerocarpa* selection (not patented).

Seeds were collected from the individual selected female plant in September of 2009 at the isolation block in Waseca, Minn., USA by the inventor. The seeds were sown by the inventor at a wholesale perennial nursery in Zeeland, Mich. in the fall of 2009 and the initial selection made in the spring of 2014 at the same nursery. The seedling ultimately given the name 'American Goldfinch' was given the breeder code of H9-19-02.

No plants of *Baptisia* 'American Goldfinch' have been sold, under this or any name, in this country or anywhere in the world, prior to the filing of this application, nor has any disclosure of the new plant been made prior to the filing of this application with the exception of that which may have been disclosed within one year of the filing of this application and was either derived directly or indirectly from the inventor.

'American Goldfinch' was initially asexually propagated by stem cuttings at a wholesale perennial nursery in Zeeland, Mich. in June of 2014. The resultant plants have demonstrated that the new plant has remained stable and true to type in successive generations of asexual propagation.

The nearest comparison plants known to the inventor are 'Lemon Meringue' U.S. Plant Pat. No. 24,280, 'Solar Flare' U.S. Plant Pat. No. 20,408 and 'Sunny Morning' U.S. Plant Pat. No. 25,479. The new plant is taller than 'Lemon Meringue' and 'Sunny Morning' and shorter than 'Solar Flare'. The flowers of 'Solar Flare' are lighter yellow blushed with orange-violet and the peduncles are more chartreuse than the new plant. The peduncles of both 'Sunny Morning' and 'Lemon Meringue' are heavily suffused with grey-purple compared with the glaucous yellow-green of the new plant. Compared with 'Lemon Meringue' the new plant produces more flowers per inflorescence and the stem of 'Lemon Meringue' is more greyed-purple.

Compared with the female parent the new plant is more mounded in habit and more floriferous. Compared to the male parent, the new plant is more floriferous with longer inflorescence and lighter yellow in flower color. The seed pods of *B. sphaerocarpa* and specifically the male parent are also spherical, much firmer and typically contain only two seeds.

The new plant differs from all *Baptisia* known to the inventor in the following combined traits:

1. Golden yellow flowers on long spikes.
2. Flowers maintain their golden yellow coloration from bud to anthesis.
3. Broad, mounded, multi-stemmed, well-branched, winter-hardy habit.
4. Glaucous, medium-green, tri-foliate foliage.

BRIEF DESCRIPTION OF THE DRAWINGS

The photographs of the 'American Goldfinch' demonstrate the unique traits of the new plant and the overall appearance. The colors are as accurate as reasonably possible with color reproductions. Variation in ambient light spectrum, source and direction may cause the appearance of minor variation in color. The accompanying photograph is of a seven-year-old plant growing in an open, full-sun, trial garden in Zeeland, Mich.

DETAILED BOTANICAL DESCRIPTION OF THE PLANT

Figure 1:
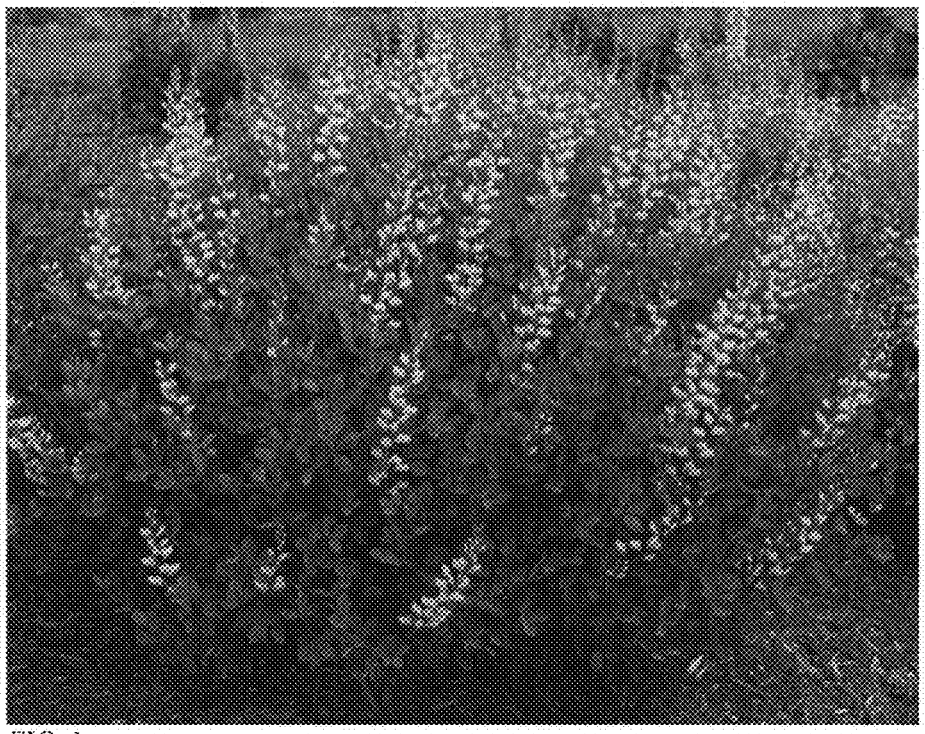
FIG. 1 shows the habit of a plant in full flower.
Figure 2:
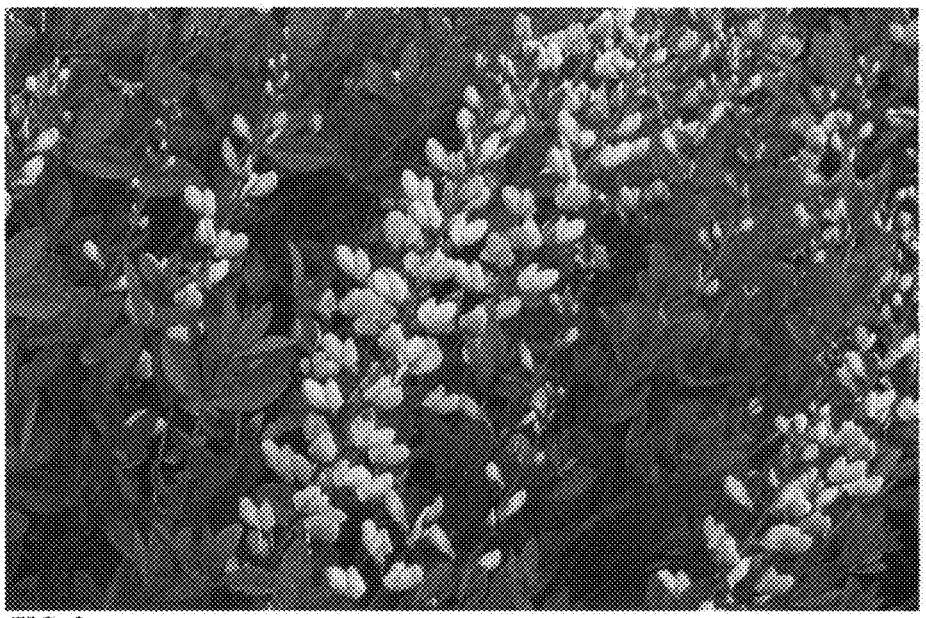
FIG. 2 shows a close-up of the flower scape.

The following is a detailed description of a seven-year-old plant of the new cultivar as grown outdoors in a trial plot at a wholesale nursery in Zeeland, Mich. Plants of the new cultivar have not been tested under all possible conditions. The phenotype may vary with changes in environment, climate, and cultural conditions without change however in the genotype. The color references are in accordance with the 2015 edition of The Royal Horticultural Society Colour Chart except where general color dictionary terms are used.

Plant habit: Perennial, compact, dense, well-branched, many-stemmed, broadly vase-shaped growth habit with long inflorescences held above the foliage;

Plant size: Stems and crown about 32.0 cm across at soil level, about 109 cm tall from soil to top of flowers and 126 cm wide just below initial flowers;

Roots: Fibrous, well-branched, long, deeply rooted;

Root color: Nearest RHS 161A;

Propagation method: Stem cuttings, rooting in about three weeks;

Growth rate: Moderate, similar to other *Baptisia;*

Stems: Rigid and upright to outwardly; highly glaucous; glabrous; cylindrical with longitudinal furrows; lower two to three nodes without leaves or branches; normally 75 to 100 stems per plant; main stem to about 12.0 mm diameter at base and 65.0 cm tall to top of inflorescence, average about 97 cm long and about 10.0 mm diameter, normally about four alternately-arranged primary branches at about 60 degree angle above horizontal, up to 30.0 cm long and 4.0 mm diameter, average for primary branches about 20.0 cm long and 3.5 mm diameter, smaller distally; and three alternately-arranged secondary branches per stem of about 12.0 cm long and 3.0 mm diameter, averaging about 10.0 cm long and 3.0 mm diameter;

Stem color: Base nearest RHS N138A;

Stem scales: At stem nodes; slightly glaucous; dehiscing to leave behind thin scar; about 4.2 cm long and 17 mm wide at base and 22 mm wide in center; frequently with apical three leaflets about 7.0 mm long and 2.0 mm wide in center of retuse apex with sharply pointed sides; truncate base;

Stem scale color: Between RHS 138C and RHS 138B before dehiscing and nearest RHS N200A after dehiscing;

Internodes: Nine on main stem to below flowers, eleven on primary branches to flowers; up to 16.0 cm apart between lowest nodes, average about 7.8 cm on main stem and primary branches;

Foliage: Alternate; ternate to palmately compound with three leaflets; outer two leaflets at about 65 to 80 degree angle to middle leaflet, increasing with leaf age; average about 5.5 cm long and about 7.5 cm wide;

Leaflet: Three, oblanceolate; apex acute, base attenuate; margins entire; petiolate; adaxial surface matte, abaxial scaberulose; center leaflet average about 7.5 cm long and 2.3 cm wide; side leaflets average about 5.0 cm long and about 2.0 cm wide;

Leaflet color: Newly expanding adaxial nearest RHS 146B and abaxial nearest RHS 146B; mature adaxial nearest RHS 137A and abaxial nearest RHS 137B;

Venation: Pinnate, glabrous, thin, not conspicuous;

Vein color: Abaxial midrib basal one-third nearest RHS 145B, remaining abaxial veins and adaxial veins same color as surrounding leaf;

Petioles: Glabrous; slightly glaucous; flattened; up to about 3.5 cm long and 2.0 mm wide at base;

Petiole color: Adaxial nearest RHS 146B, abaxial nearest RHS 146C;

Stipules: Narrowly lanceolate to trifurcate, acute apex with base truncate to stem; average about 22.0 mm long and 17.0 mm wide at base and 22.0 mm wide in middle; side lobes 5.0 mm long and 4.0 mm wide at base, center lobe about 7.0 mm long and 2.0 mm wide at base; with largest stipules below primary branches and decreasing distally and on secondary branches;

Stipule color: Nearest RHS 138A both surfaces;

Inflorescence: Main stem about 32.0 cm long and 8.0 cm wide;

Flower: Zygomorphic, papilionaceous, non-secund, held at about 45 degree angle above horizontal when open; about 51 flowers per main raceme and about 15 per secondary branch; seasonally effective for about 3 to 4 weeks beginning in late May in Zeeland, Mich.; individual flower remain effective and on raceme for about four days; individually about 2.5 cm long, 1.8 cm tall and 1.4 cm wide at tallest and widest portions; an upper banner, a lower keel made up of two lobes folded around gynoecium and androecium; and two lateral wings or alae laterally appressed against keel;

Flower fragrance: None detected;

Peduncle: Rounded with vertical ridges and furrows; glaucous; glabrous; from first flower to apex about 42 cm long; diameter at the base of first flower about 5.0 mm and about 2 mm diameter at the apex;

Peduncle color: Nearest RHS 151A;

Pedicel: Terete, glabrous, slightly glaucous; about 10.0 mm long and 1.0 mm diameter; angle upwardly to slightly outwardly;

Pedicel color: Blend of N189A and RHS N187A;

Calyx: Campanulate; glaucous; glabrous; five sepals fused in basal 5.0 mm with acute apices; about 7.5 mm long and 10.0 mm across;

Sepals: Five; fused in basal 5.0 mm, acute apices; margins entire; distal two lobes only dissected about 1.0 mm and side and lower lobes dissected about 3.0 mm deep; distal, side and proximal sepals about 3.0 mm to 4.0 mm wide at fusion; side sepals reflexed, distal and proximal sepals flat; persists after petal drop;

Sepal color: Adaxial nearest RHS 146D; abaxial nearest RHS 146D with slight blushing of nearest RHS 183C in distal regions with more intense light;

Buds one day prior to anthesis: Oblong ellipsoid; flatted vertically; about 22.0 mm long and 11.0 mm tall and 6.0 mm wide near base;

Bud color: About two days prior to opening nearest RHS 1B proximally and nearest RHS 1A distally;

Petals: Five; with a lower fused keel, an upper banner, and two lateral wings or alae; keel comprised of two sections that are folded around stamens and pistil;

*Banner petal*.—Conduplicate, curved upward and backward and pinched in the middle; apex retuse, base claw-like, margin entire; about 18.0 mm long, 16.0 mm wide at broadest position; claw-like base 5.0 mm long and narrowing to 1.0 mm at base and expanding to 5.0 mm wide before blade; color adaxial blade toward perimeter nearest RHS 1A, center blade speckled with nearest RHS N187A; adaxial claw nearest RHS 150C; abaxial blade nearest RHS 2A, claw and center of proximal blade nearest RHS 151C.

*Keel*.—Comprised of two main lobes that are folded around stamens and pistil; fused about 4.0 mm from base; apex rounded; base aciculate; claw curved upward, about 5.0 mm long and 1.0 mm across at base; about 19.0 mm long with blade 9.0 mm across near middle; color abaxial blade between RHS 1C and RHS 1D; claw color nearest RHS 145C; abaxial blade margin between RHS 1B and RHS 1C with proximal and central portion between RHS 1C and RHS 1D.

*Alae*.—Two; papilionaceous corolla appendage with rounded apex and claw-like base; apex rounded; blade base auriculate; claw base curved upwardly, claw about 5.0 mm long and 1.0 mm across at base; blade about 17.0 mm long and 8.0 mm wide in middle; total alae length with claw 20.0 mm long; with 2.0 mm lobe pointing toward base and about one-third of the way from base; alae adaxial blade color between RHS 1A and RHS 1B, adaxial claw nearest RHS 145C; abaxial blade color between RHS 1A and RHS 1B with claw nearest RHS 145C.

Receptacle: Disk-shaped, about 3.5 mm diameter and 1.5 mm depth; color nearest RHS 139A;

Gynoecium: One, with superior ovary;

*Pistil*.—Stalked; glabrous; about 20.7 mm long.

*Style*.—Terete; tapering, narrowing distally; about 10.0 mm long and less than 1.0 mm diameter; color nearest RHS 145C.

*Stigma*.—Less than 0.5 mm diameter; color nearest RHS 155A.

*Ovary*.—Superior suspended by stipe; terete; about 5.0 mm long and about 1.5 mm in diameter; color nearest RHS 143C.

*Stipe*.—Terete; about 4.0 mm long and 0.7 mm diameter; color nearest RHS 145A.

Androecium:

*Stamens*.—Ten, not united, curved upwardly; naturally to about 17.0 mm long and 1.0 mm diameter.

*Filament*.—Terete; as straightened to about 20.0 mm long and about 1.0 mm in diameter; color nearest RHS 145C.

*Anther*.—Dorsifixed, ellipsoidal; about 2.0 mm long and 1.5 mm wide; color nearest RHS 16A.

*Pollen*.—Spherical; abundant; color nearest RHS 17A.

Fruit: Bivalve inflated pod; glabrous; ellipsoidal; with rounded based and rounded beaked apex; about 19.0 mm long, 13.0 mm across and 10.0 mm tall; with thin linear terminal beak about 3.0 mm to 4.0 mm long and about 0.3 mm thick;

Fruit color: At maturity blotchy with portions nearest N200A and RHS 199C;

Seeds: Typically about 10 per flower (open pollinated); reniform; semi-microscopically muriculate; about 4.0 mm long, 3.0 mm across and 1.5 mm thick; color between RHS 166A and RHS 166B;

Hardiness: To USDA zones 4 to 9; tolerant of heavy clay or light loamy-sand soils; able to withstand drought conditions once established;

Diseases: Susceptibility or resistance to diseases beyond that typically found in other false indigo plants has not been observed; The new plant has not been found to show any susceptibility or resistance to any diseases or pest that might be common to other False Indigo plants.

It is claimed:

1. A new and distinct cultivar of hardy herbaceous false indigo plant named *Baptisia* 'American Goldfinch' as herein described and illustrated.

* * * * *